(12) United States Patent
Choudhary et al.

(10) Patent No.: US 10,426,806 B1
(45) Date of Patent: Oct. 1, 2019

(54) **ANTI-OBESITY EFFECT OF *BORAGO OFFICINALIS* LINN. EXTRACTS TO PREVENT AND TREAT METABOLIC DISORDERS**

(71) Applicants: Muhammad Iqbal Choudhary, Karachi (PK); Sammer Yousuf, Karachi (PK); Misha Siddiqui, Karachi (PK); Madiha Mukhtar, Karachi (PK)

(72) Inventors: Muhammad Iqbal Choudhary, Karachi (PK); Sammer Yousuf, Karachi (PK); Misha Siddiqui, Karachi (PK); Madiha Mukhtar, Karachi (PK)

(*) Notice: Subject to any disclaimer, the term of this patent is extended or adjusted under 35 U.S.C. 154(b) by 0 days.

(21) Appl. No.: 16/007,130

(22) Filed: Jun. 13, 2018

(51) Int. Cl.
*A61K 36/00* (2006.01)
*A61K 36/30* (2006.01)
*A61P 3/10* (2006.01)
*A61P 3/04* (2006.01)

(52) U.S. Cl.
CPC ............... *A61K 36/30* (2013.01); *A61P 3/04* (2018.01); *A61P 3/10* (2018.01)

(58) Field of Classification Search
CPC ........................................................ A61K 36/00
USPC .......................................................... 424/725
See application file for complete search history.

(56) References Cited

FOREIGN PATENT DOCUMENTS

WO    WO2015072674 A1 *  5/2015

* cited by examiner

*Primary Examiner* — Michael V Meller
(74) *Attorney, Agent, or Firm* — Sarfaraz K. Niazi

(57) ABSTRACT

The present invention relates to reducing insulin resistance by administering an oral dose of an ethanolic extracts of *Borago officinalis* Linn., wherein the treatment further reduces dyslipidemia, hypertension, cardiovascular diseases, and resistance to insulin.

1 Claim, 10 Drawing Sheets

(a) (b) (c)
(d) (e) (f)

(a)

(b)

(c)

(d)

(e)

(f)

(a) (b) (c)

(d) (e) (f)

ANTI-OBESITY EFFECT OF *BORAGO OFFICINALIS* LINN. EXTRACTS TO PREVENT AND TREAT METABOLIC DISORDERS

FIELD OF THE INVENTION

The present invention relates to anti-obesity use of non-toxic ethanolic extracts of *Borago officinalis* Linn., wherein the treatment further reduces dyslipidemia, hypertension, cardiovascular diseases, and resistance to insulin.

BRIEF SUMMARY OF INVENTION

The effect of ethanolic extract of *B. officinalis* Linn. on body weights, food intake, biochemical parameters, such as fasting blood glucose, lipid profile, serum insulin levels, and serum leptin levels, and morphological changes in the liver and adipose tissue of high-fat diet-induced obese rat were studied in vivo.

Obese male Wistar rat models were established by feeding high-fat diets for a period of 16 weeks.

The anti-obesity and anti-dyslipidemic effects of *B. officinalis* was studied at two different doses, i.e. 150 mg/kg/day, and 300 mg/kg/day.

Oral application of ethanolic extract of *B. officinalis* at a dose of 300 mg/kg caused a significant reduction in the body weight of animals, along with ameliorated dyslipidemia and lowered serum triglyceride, total cholesterol, LDL and VLDL (very low density lipoprotein) levels.

The plant extract (300 mg/kg) further improved the insulin sensitivity, i.e., significantly reduced the fasting blood glucose and serum insulin levels, as well as lowered the lipase levels. Morphological studies by light microscopy displayed a dose-dependent recovery in the hepatic steatosis, caused by prolonged feeding of high-fat diets to the rats.

The application of plant extract caused no changes in the serum urea, creatinine, serum glutamic pyruvic transaminase (SGPT), aspartate aminotransferase (ALT), alkaline phosphatase (ALP), and total and direct bilirubin levels. This indicates that the extract did not exert any adverse effects on renal, and liver functions.

The findings clearly demonstrate the anti-obesity potential of ethanolic extract of *B. officinalis* at a dose of 300 mg/kg/day. It also shows significant effect on leptin level. The extract significantly decreases the insulin levels. It shows no toxic effect on hepatic and renal functions on rats. It reversed the dyslipidemia in obese rats. It also positively affects other biochemical parameters, such as lowering the cholesterol, triglycerides, LDL, and VLDL levels with significant abilities of reversal of dyslipidemia and insulin resistance in vivo (high-fat diet induced obese rat models).

DETAILED DESCRIPTION OF THE INVENTION

Figure 1:
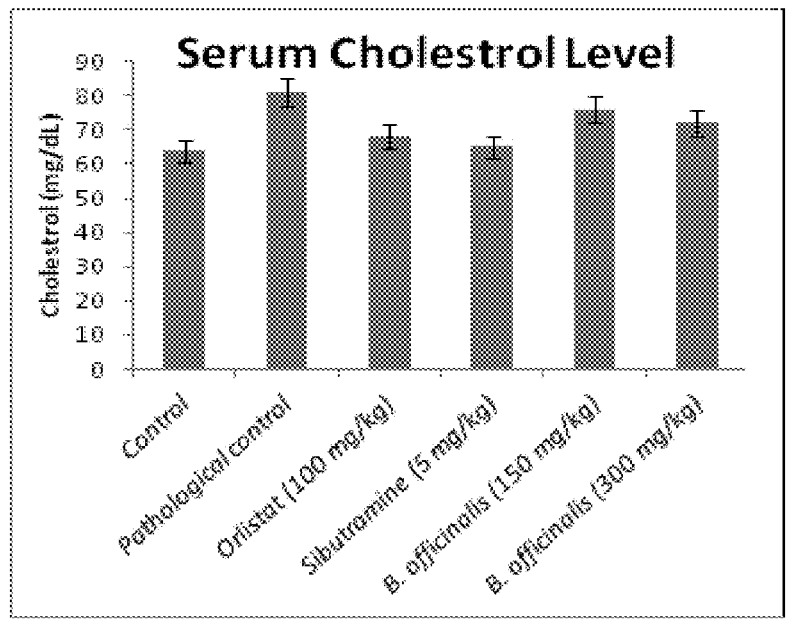
FIG. 1 depicts the serum total cholestrol levels after 8 weeks of preventive studies of high fat diet rats with *Borago officinalis* extracts (150, and 300 mg/kg). Values are expressed as mean±SEM.
Figure 2:
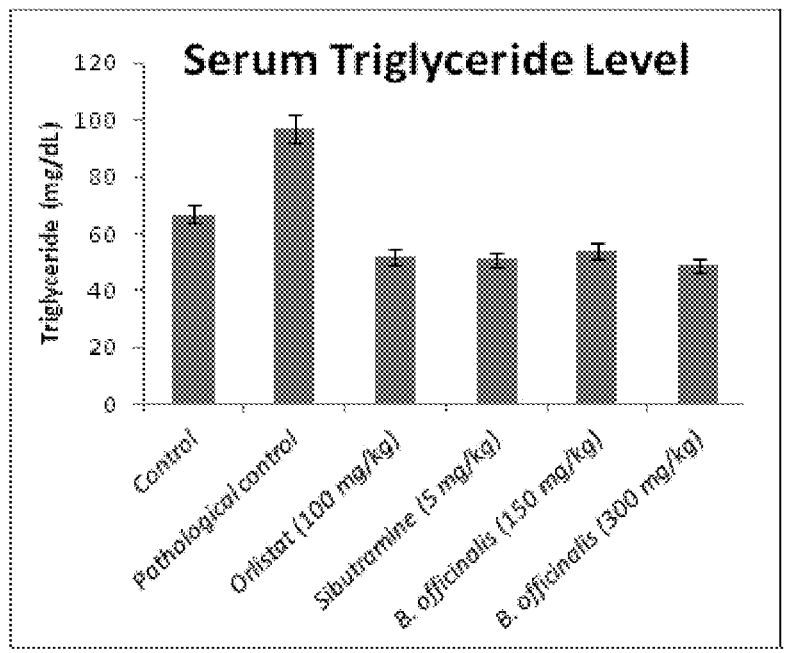
FIG. 2 depicts the serum triglyceride levels after 8 weeks of preventive studies of high fat diet rats with *Borago officinalis* extracts (150, and 300 mg/kg). Values are expressed as mean±SEM.
Figure 3:
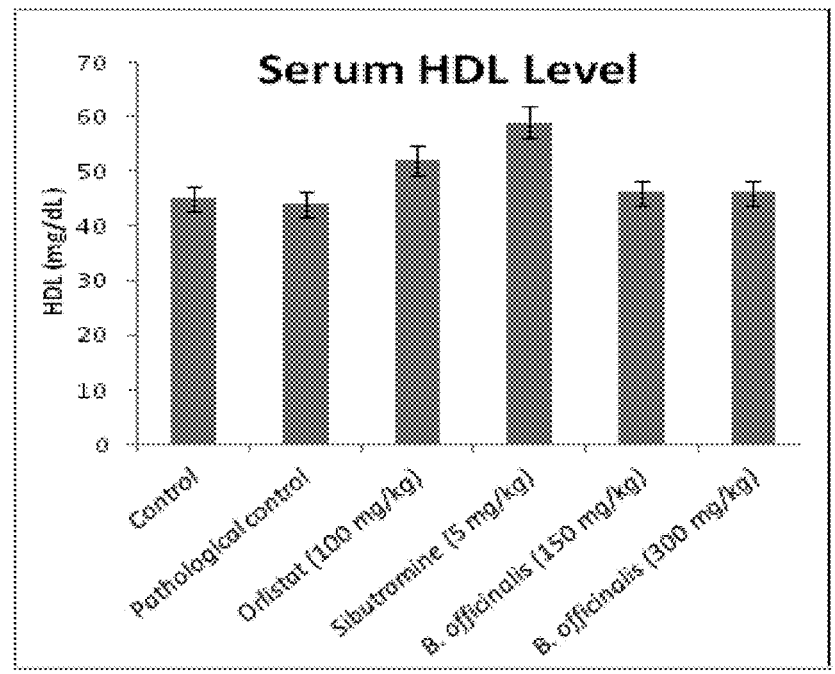
FIG. 3 depicts the serum HDL levels after 8 weeks of preventive studies of high fat diet rats with *Borago officinalis* extracts (150, and 300 mg/kg). Values are expressed as mean±SEM.
Figure 4:
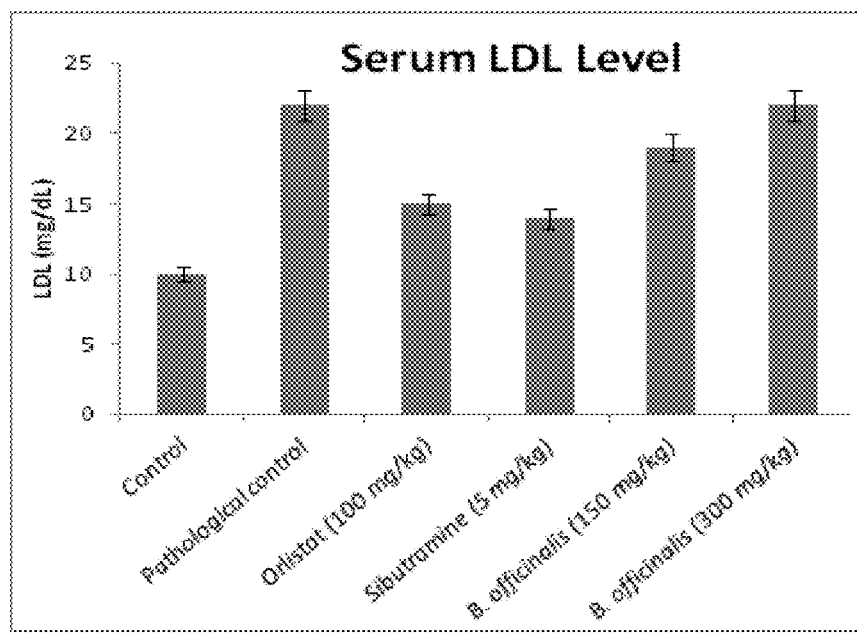
FIG. 4 depicts the serum LDL levels after 8 weeks of preventive studies of high fat diet rats with *Borago officinalis* extracts (150, and 300 mg/kg). Values are expressed as mean±SEM.

Obesity is a condition in which the natural energy reserve, stored in the fatty tissues of humans and other mammals, is increased to a point where it is a risk factor for certain health conditions or increased mortality. Excessive body weight has been shown to predispose to various diseases, particularly cardiovascular diseases, diabetes mellitus type 2, sleep apnea, and osteoarthritis. Obesity is an individual clinical condition, and is also increasingly viewed as a serious public health problem globally.

The term herb refers to a plant used for medicinal purposes and is oldest form of healthcare. Since the beginning of human civilization herbs have been used for treating various ailments. In recent years, there has been an increasing interest by researchers worldwide in the medicinal uses of traditional herbs. Studies shows about 25% of the drugs prescribed worldwide are derived from plants.

A number of rodent models have been developed for the study of the pathogenesis related to the metabolic syndrome. These studies demonstrated that high-fat diet promotes the whole-body insulin resistance, and hyperglycemia. The effect of hyperglycemia and insulin resistance on liver physiology, muscle, and insulin signal transduction has also been examined by researchers. These studies indicate that the high-fat diet can be used to cause metabolic syndrome with insulin resistance, and compromised β-cell functions in a rodent model. High-fat diet, fed to rodents, increases triglyceride levels in muscles followed by insulin resistance, a state equivalent to metabolic syndrome in humans. Wistar rats fed with high-fat diet are known to develop obesity, hypertension, dyslipidemia, glucose intolerance, and hyperinsulinemia; collectively called metabolic syndrome.

Medicinal uses of plants arise from ethnobotanical and ethnopharmacological approaches that involve their therapeutic use in the prevention and treatment of numerous diseases. These approaches include popular knowledge; thus the traditional missing has become something of great importance to science. These approaches also contribute to the selection of species to be studied and the development of phytotherapeutic medicines based on ethnopharmacological uses.

*Borago officinalis* L., belongs to the family Boraginaceae, commonly known as Gul gaozaban or Borage, is an annual herb with nutritional value. It is extensively used in traditional medicines and for culinary purposes in some countries. Borage is cultivated around the world but is native to Europe, North Africa, and Asia. Borage products, mainly seeds, oil, flowers, and leaves are used for medicinal, and culinary purposes.

*B. officinalis* might exert its anti-obesity action through the inhibition of intestinal absorption of dietary fat, its hypophagic activity, and its hypolipidemic activity.

Materials and Methods

Preparation of Extract and Standard Drugs

The aerial parts of *Borago officinalis* (10 kg) were purchased from local herbal market in Karachi (Pakistan), identified by plant taxonomist of Department of Botany, University of Karachi, and a voucher specimen (G.H. No: 68223) has been deposited in the herbarium. The air dried *Borago officinalis* (10 kg) were crushed, and soaked in ethanol (10 L). After 5 days, the plants were filtered, followed by evaporation under reduced pressures to obtain crude ethanolic extracts (450 g). The crude extracts were completely dried under reduced pressure on rota vapor, and stored at 4° C.

The crude extracts of *B. officinalis* were suspended in distilled water before its administration to the rat models. Orlistat and Sibutramine were used as standard anti-obesity drugs at doses of 100 mg/kg, and 5 mg/kg, respectively (dissolved in distilled water).

Toxicity of ethanolic extracts of *Borago officinalis* were evaluated for the measurement of $LD_{50}$ values. Animals were given oral doses, ranging between 10 mg/kg to 1000 mg/kg, and observed for 48 hrs.

Animals

Thirty male Wistar rats (210-220 g) were obtained from the animal house facility of Dr. Panjwani Center for Molecular Medicine and Drug Research (ICCBS). All animals were kept under standard conditions of temperature and humidity with a 12 h light/dark cycle. This study was approved by the Ethical Committee of International Center for Chemical and Biological Sciences (Protocol #: 2015-0011). After one week of acclimation period, rats were randomly divided into two groups. The control group was fed with normal diet (D12450B, Research Diets, USA), whereas the other groups were fed with high-fat diet (D12451, Research Diets, USA) for a period of 16-week. The compositions of the diet are given in Table-1. After 10 weeks, biochemical parameters were evaluated regularly to establish whether the model has developed the symptoms of weight gain and metabolic syndrome.

Two types of diets were used in this study, i.e. low fat diet, and high fat diet. These diets were acquired from Research Diets, New Brunswick, N.J., USA.

The low-fat diet contains 20% of energy as proteins, 70% of energy as carbohydrates, and 10% of energy as fat.

The high-fat diet contains 20% of energy as protein, 35% as carbohydrates, and 45% as fat (of total energy, % kcal), as shown in Table-1.

TABLE 1

Composition of the low, and high-fat diets.

| | D12450B (Normal Diet) | | D12451 (High fat diet) | |
|---|---|---|---|---|
| | gm % | kcal % | gm % | kcal % |
| Protein | 19.2 | 20 | 24 | 20 |
| Carbohydrate | 67.3 | 70 | 41 | 35 |
| Fat | 4.3 | 10 | 24 | 45 |
| kcal/gm | 3.85 | | 4.73 | |

Extract Supplementation

After a period of 16 weeks, the group of rats on high fat diet (HF) have developed symptoms of metabolic disorders, along with insulin resistance. The HF fed rats were then sub-divided into four groups of three rats each, i.e. Group 1 (PA), Control; animals in this group received LFD, and distilled water. Group 2, Pathological control (PC); animals in this group received HFD, and distilled water. Group 3 (PO); animals in this group received HFD, and standard drug Orlistat (100 mg/kg/day). Group 4 (PS); animals in this group received HFD, and standard drug Sibutramine (5 mg/kg/day). Group 5 (PC1); animals in this group received HFD, and *B. officinalis* extract (150 mg/kg/day). Group 6 (PC2); animals in this group received HFD, and *B. officinalis* extract (300 mg/kg/day).

Whereas for therapeutic studies the animal groups were further sub-divided into following groups which are as follow: Group 1 (TA), Control; animals in this group received LFD, and distilled water. Group 2 (TC), Pathological control; animals in this group received HFD, and distilled water. Groups 3 (TO), High fat diet induced obese animals in this group received standard drug Orlistat (100 mg/kg/day). Group 4 (TS): High fat diet induced obese animals in this group received standard drug Sibutramine (5 mg/kg/day). Group 5 (TC1): High fat diet induced obese animals in this group received *B. officinalis* extract (150 mg/kg/day). Group 6 (TC2): High fat diet induced obese animals in this group received *B. officinalis* extract (300 mg/kg/day).

Food Intake and Body Weights

Body weights were recorded weekly throughout the experiment. The food intake was calculated by using following formula, as described by Ghezzi et al, 2012:

$$\text{Food intake} = \frac{\text{Daily food intake (g)}}{\Sigma \text{ Body weight of rats in each cage (g)}}$$

Blood and Tissue Collections and Sample Preparation

For biochemical analysis after 16 weeks of experimental diet, the blood samples were taken from the tail vein after an overnight fast, whereas after 12 weeks of treatment period, rats were subjected to anesthesia, and blood was drawn by cardiac puncture. Liver and pancreas samples were prepared and stained with hematoxylin and eosin; the liver was excised and fixed in buffered formalin. The sectioned liver tissue segments were stained with hematoxylin-eosin (H-E), and observed under light microscope.

Biochemical Measurements

Blood glucose, serum insulin, total cholesterol, triglycerides, HDL, LDL, very low density lipoproteins (LDG-LP), urea, creatinine, aspartate aminotransferase (ALT), alkaline phosphatase (ALP), serum glutamic pyruvic transaminase (SGPT), and direct and total bilirubin were estimated. Fasting blood glucose levels were measured using glucometer (AccuChek Performa, Australia). Fasting insulin levels were quantified using ultra sensitive rat insulin ELISA kit (Crystal Chem, Downers Grove, USA). Insulin sensitivity was evaluated using Homeostatic Model Assessment (HOMA). Serum total cholesterol, triglycerides, HDL, LDL, VLDL, urea, creatinine, AST, ALP, SGPT, and direct and total bilirubin were analyzed using automatic analyzer (Hitachi, Roche Diagnostics 902, Tokyo, Japan).

Statistical Analysis

All data are expressed as mean±SEM. Significance was determined using the two-tailed unpaired student's t test or ANOVA. Differences>less than 0.05 were considered significant.

Results and Discussion (A) Preventive Study

Effects of Plant Extract Supplementation on Physical and Biochemical Parameters: Food Intake During preventive studies an increase in the food intake was observed by the group of animals fed on *B. officinalis* extract (PC2) at a dose of 300 mg/kg, however it seems to be comparable to that of control group (PC, animal on low fat diet), (Table-2).

TABLE 2

Food Intake (g/100 g) of rats during 8 weeks of preventive studies.

| Groups (Codes) | Average Food intake (g/100 g) |
|---|---|
| Control (PA) | 5.62 |
| Pathological control (PC) | 6.23 |
| Orlistat (100 mg/kg) (PO) | 4.23 |
| Sibutramine (5 mg/kg) (PS) | 5.34 |
| *B. officinalis* extract (150 mg/kg) (PC1) | 5.11 |
| *B. officinalis* extract (300 mg/kg) (PC2) | 4.80 |

Effect of Plant Extract Supplementation on Physical and Biochemical Parameters:

Body Weight

A significant reduction in body weight of group PC2 (fed with high diet and *B. officinalis* extract at a dosage of 300 mg/kg) was observed as compared to group PC1 (fed with high diet and *B. officinalis* extract at a dose of 150 mg/kg), and pathological control (PC) (Table-3).

TABLE 3

Average body weight (g) of rats during 8 weeks of preventive studies.

| Groups | Average body weight (g) |
|---|---|
| Control (PA) | 232 ± 0.07 |
| Pathological control (PC) | 300 ± 0.07 |
| Orlistat (100 mg/kg) (PO) | 256 ± 0.10 |
| Sibutramine (5 mg/kg) (PS) | 251 ± 0.11 |
| *B. officinalis* extract (150 mg/kg) (PC1) | 262 ± 0.14 |
| *B. officinalis* extract (300 mg/kg) (PC2) | 249 ± 0.16 |

Biochemical Parameters

Lipid Profile

Both groups (PC1, and PC2) receiving 150 and taking 300 mg/kg of *B. officinalis* extract, respectively, showed significant decrease in serum levels of total cholesterol, triglyceride, LDL, and VLDL levels, as compared to the pathological control (Table-4, FIGS. 1, 2, 3, and 4, respectively).

Figure 5:
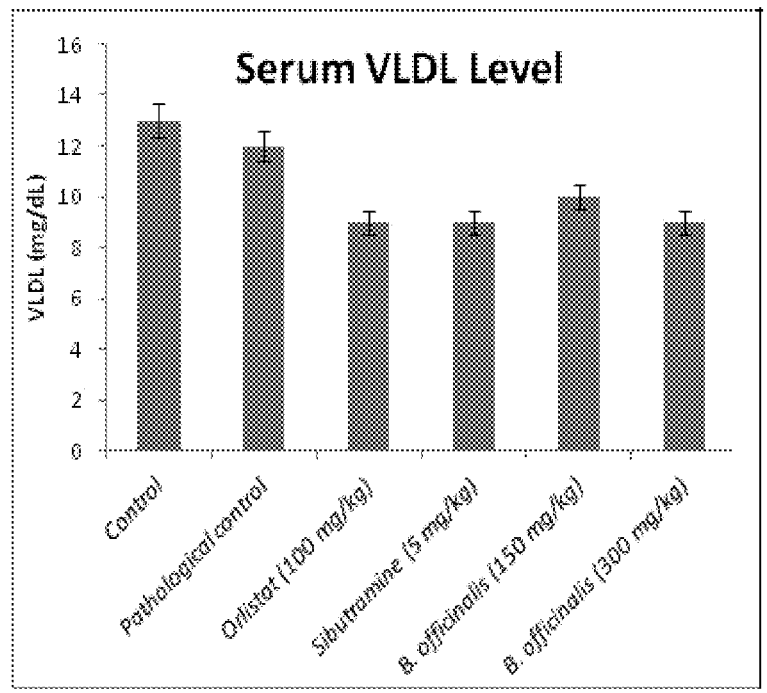
FIG. 5 depicts the serum VLDL levels after 8 weeks of preventive studies of high fat diet rats with *Borago officinalis* extracts (150, and 300 mg/kg). Values are expressed as mean±SEM.

However, *Borago officinalis* extracts significant increase in HDL level observed both in groups PC1 and PC2 as compared to pathological control (PC). This further supported the antiobesity effect of *C. latifolia* with the ability to reverse dyslipidemia (Table-4, FIG. 5).

TABLE 4

Biochemical parameters of rats during 8 weeks of preventive studies.

| Groups | Cholestrol (mg/dL) | Tri-glyceride (mg/dL) | HDL (mg/dL) | LDL (mg/dL) | VLDL (mg/dL) |
|---|---|---|---|---|---|
| Control (PA) | 64 ± 2.62 | 67 ± 0.09 | 45 ± 0.56 | 10 ± 1.36 | 13 ± 2.04 |
| Pathological control (PC) | 81 ± 0.18 | 97 ± 0.05 | 44 ± 0.31 | 22 ± 1.43 | 12 ± 3.47 |
| Orlistat (100 mg/kg) (PO) | 68 ± 3.66 | 52 ± 0.16 | 52 ± 3.04 | 15 ± 0.41 | 9 ± 0.87 |
| Sibutramine (5 mg/kg) (PS) | 65 ± 0.13 | 51 ± 0.19 | 59 ± 0.16 | 14 ± 0.68 | 9 ± 0.8 |
| *B. officinalis* extract (150 mg/kg) (PC1) | 76 ± 0.48 | 54 ± 0.12 | 46 ± 0.87 | 19 ± 0.76 | 10 ± 0.61 |
| *B. officinalis* extract (30 mg/kg) (PC2) | 72 ± 0.23 | 49 ± 0.20 | 46 ± 0.31 | 22 ± 0.98 | 9 ± 1.08 |

Fasting Blood Glucose Level

Figure 6:
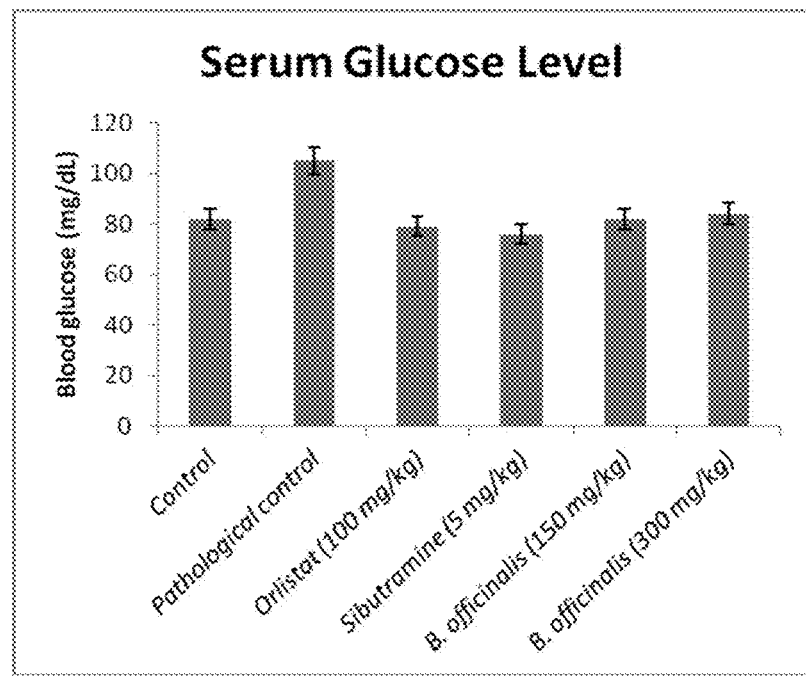
FIG. 6 depicts the fasting blood glucose levels after 8 weeks of preventive studies of high fat diet rats model with *Borago officinalis* extracts (150, and 300 mg/kg). Values are expressed as mean±SEM.

Significant reduction in fasting blood glucose levels was seen in groups PC1 and PC2 as compared to the pathological control (PC) (Table-5, FIG. 6). The results found to be comparable to the control group (PA). This further supported that *B. officinalis* extract has hypoglycemic activity to control the increased blood glucose level, and therefore may have a potential to treat diabetes.

TABLE 5

Fasting Blood Glucose Level of Preventive Studies.

| Groups | FBG (mg/dL) |
| --- | --- |
| Control (PA) | 82 ± 1.54 |
| Pathalogical control (PC) | 105 ± 0.20 |
| Orlistat (100 mg/kg) (PO) | 79 ± 1.04 |
| Sibutramine (5 mg/kg) (PS) | 76 ± 2.12 |
| *B. officinalis* extract (150 mg/kg) (PC1) | 82 ± 1.06 |
| *B. officinalis* extract (300 mg/kg) (PC2) | 84 ± 1.58 |

Histopathology of Liver

Figure 7:
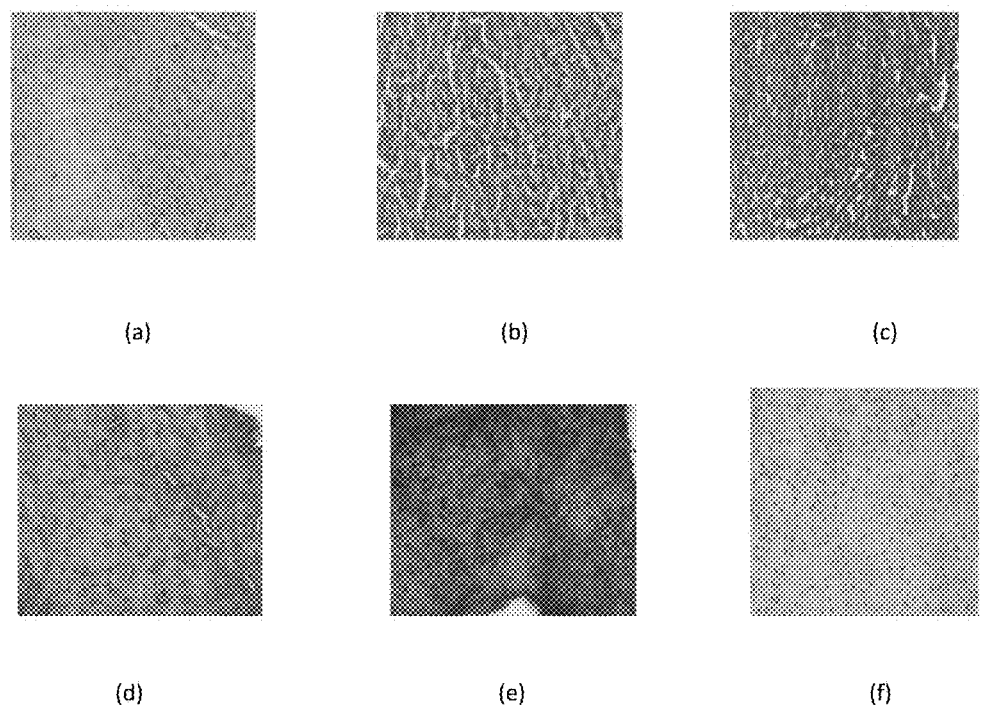
FIG. 7 depicts the histological examination of liver tissues of high fat diet rats (preventive studies) with hematoxylin and eosin (H & E) staining; magnification 20×. Image (a) Control, (b) Pathological control, (c) Standard Orlistat (100 mg/kg), (d) Standard Sibutramine (5 mg/kg), (e) *Borago officinalis* EtOH extract (150 mg/kg), and (f) *Borago officinalis* EtOH extract (300 mg/kg).

Hepatic morphological changes were examined microscopically with H & E staining. An excessive fat accumulation was seen in hepatocytes of PC (pathological control group) as compared to Orlistat and Sibutramine groups. Both PC1 (treated with *Borago officinalis* extract at a dose of 150 mg/kg group), and as PC2 (*Borago officinalis* extract at a dose of 300 mg/kg) group showed results comparable to that control group indicating that *Borago officinalis* extracts are also decreasing the accumulation of fats in liver. With the help of liver cell images, it was concluded that severe steatosis occurs only in pathological control group, as shown in FIG. 7.

(B) Therapeutic Study

In therapeutic study, we investigated the capacity of *B. officinalis* extracts to reduce the weight of high fat diet induced obese rats, and to improve the key biochemical parameters in metabolic disorders. The ability to reduce the gained weight by high fat diet induced obese rats was observed at two different doses of *B. officinalis* i.e. 150 mg/kg, and 300 mg/kg.

Establishment of Obese Rat Model

Food Intake and Body Weight

Obesity was induced in normal rats by providing them a high-fat diet for 16 weeks. When we compared the food intake of both groups (i.e. low fat diet and high-fat diet), we observed that there was no significant difference in the food intake of rats, as shown in Table-6.

TABLE 6

Daily food intake (mean ± SEM) by rats.

| Groups | Food intake (gm/100 gm) |
| --- | --- |
| Low-fat diet group (LFD) | 4.69 ± 0.19 |
| High-fat diet (HFD) | 3.82 ± 0.13 |

Figure 8:
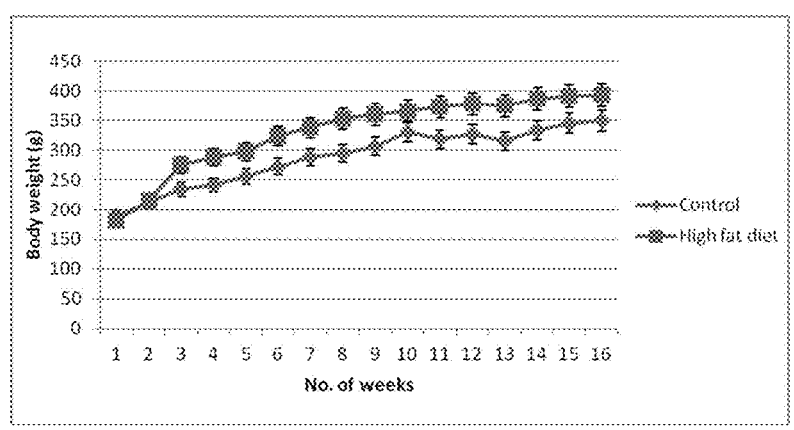
FIG. 8 depicts the change in body weights of control and high fat diet supplemented rats during 16 weeks of experimental diet.
Figure 9:
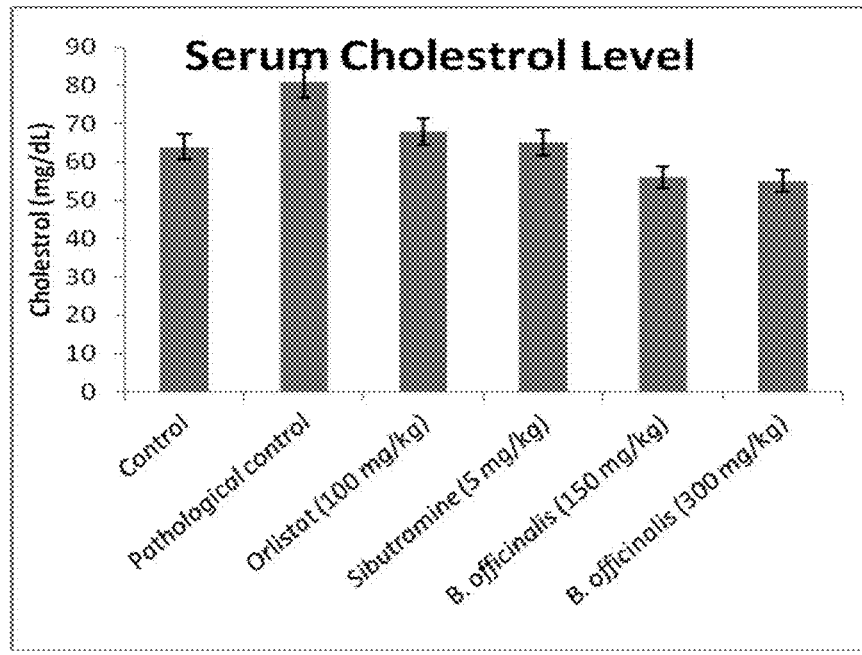
FIG. 9 depicts the serum total cholesterol levels after 12 weeks of therapeutic studies on high-fat diet induced-obese rats model with *Borago officinalis* extracts (150, and 300 mg/kg). Values are expressed as mean±SEM.
Figure 10:
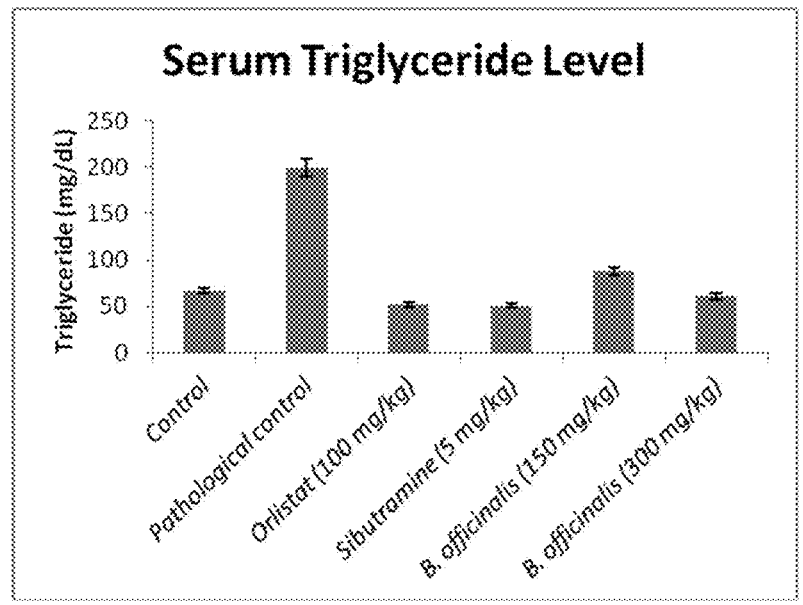
FIG. 10 depicts the serum triglycerides levels after 12 weeks of therapeutic studies on high-fat diet induced-obese rats model with *Borago officinalis* extracts (150, and 300 mg/kg). Values are expressed as mean±SEM.
Figure 11:
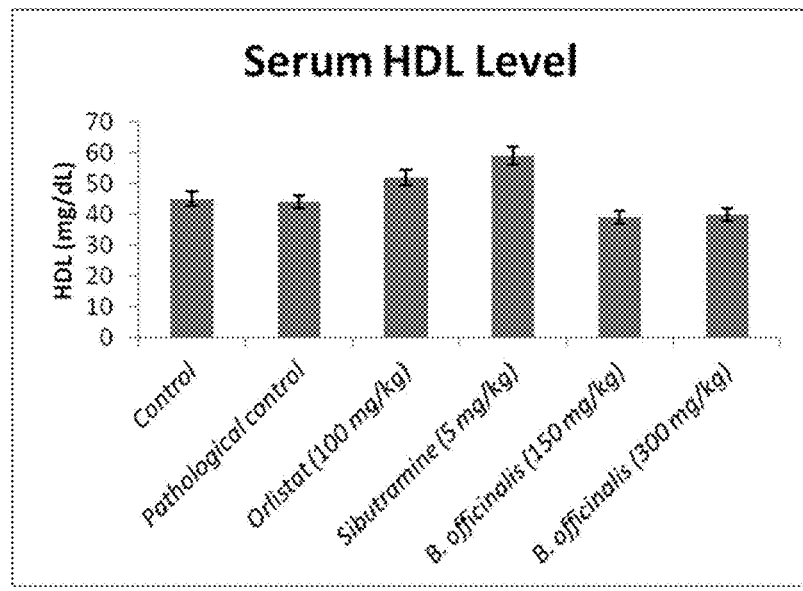
FIG. 11 depicts the serum HDL levels after 12 weeks of therapeutic studies on high-fat diet induced-obese rats model with *Borago officinalis* extracts (150, and 300 mg/kg). Values are expressed as mean±SEM.
Figure 12:
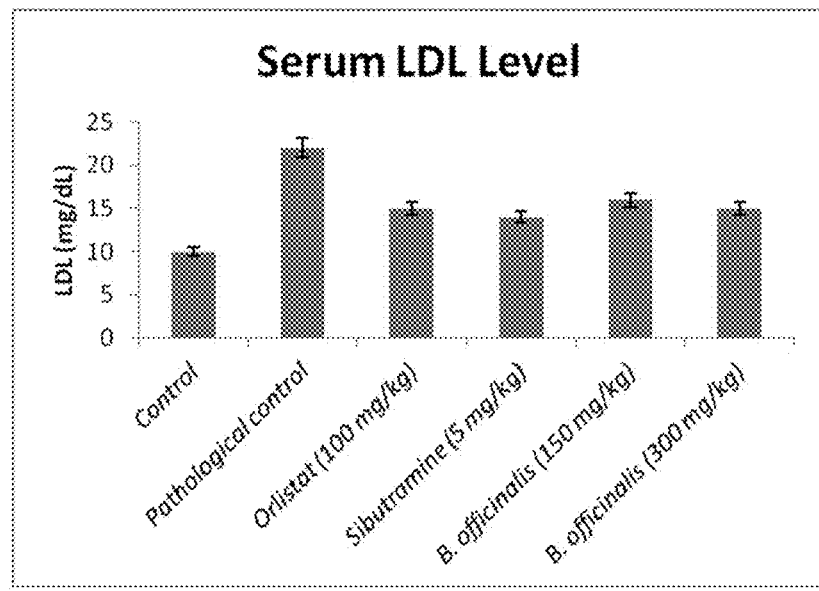
FIG. 12 depicts the serum LDL levels after 12 weeks of therapeutic studies on high-fat diet induced-obese rats model with *Borago officinalis* extracts (150, and 300 mg/kg). Values are expressed as mean±SEM.
Figure 13:
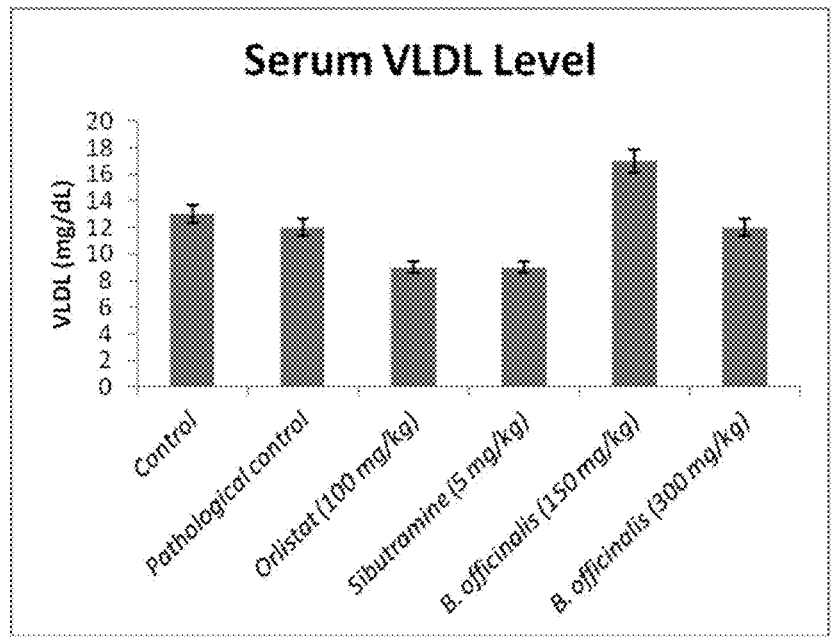
FIG. 13 depicts serum VLDL levels after 12 weeks of therapeutic studies on high-fat diet induced-obese rats model with *Borago officinalis* extracts (150, and 300 mg/kg). Values are expressed as mean±SEM.

A clear change in body weight we seen by providing a high-fat diet for 16 weeks to animals. We observed a gradual increase in body weight, as compared to the low-fat diet group, as shown in FIG. 8.

Lipid Profile

The successful establishment of the animal model was validated based on biochemical parameters, such as fasting blood glucose, serum cholesterol, triglyceride, VLDL, HDL and LDL levels.

Results showed that total cholesterol, triglyceride, LDL, and VLDL levels in serum significantly decreased in low-fat diet group, as compared to the control group, whereas the HDL level was decreased in high-fat fed rats, as compared to the control rats group. These changes indicated a condition of dyslipidemia in rats fed with high-fat diet. The fasting blood glucose level was significantly increased in high-fat diet group, as compared to the control group as shown in Table-7.

TABLE 7

Effect of normal diet and high-fat diet on the serum glucose and serum lipid profile after 16 weeks of experimental diet to rats.

| Serum parameters | Low fat diet group (LFD) | High fat diet group (HFD) |
| --- | --- | --- |
| FBG (mg/dL) | 83 ± 0.47 | 92.5 ± 3.76 |
| Cholesterol (mg/dL) | 79.4 ± 7.26 | 80.33 ± 3.41 |
| Triglyceride (mg/dL) | 168 ± 4.61 | 204 ± 0.03 |
| HDL (mg/dL) | 51.16 ± 2.70 | 37.6 ± 1.94 |
| LDL (mg/dL) | 25 ± 2.7 | 27.25 ± 3.11 |
| VLDL (mg/dL) | 10.5 ± 2.04 | 33.4 ± 8.02 |

Effect of Plant Extract Supplementation on Physical and Biochemical Parameters: Food Intake.

Obese rats were treated with *Borago officinalis* extracts, at two different doses i.e. 150 mg/kg, and 300 mg/kg of body weight for 12 weeks. During these 12 weeks they were also fed HFD. Results showed a decrease in the average food intake of rats in the Orlistat (TO), Sibutramine (TS), and *Borago officinalis* extracts (TC1 and TC2) treated groups, as shown in Table-8.

TABLE 8

Average food intake of rats during 12 weeks of treatment period.

| Groups | Average Food Intake (g/100 g) |
| --- | --- |
| Control (TA) | 3.40 |
| Pathological control (TP) | 5.68 |
| Orlistat (100 mg/kg) (TO) | 3.18 |
| Sibutramine (5 mg/kg) (TS) | 4.20 |
| *B. officinalis* extract (150 mg/kg) (TC1) | 3.20 |
| *B. officinalis* extract (300 mg/kg) (TC2) | 3.55 |

Effect of Plant Extract Supplementation on Physical and Biochemical Parameters:

Body Weights

During 12 weeks of treatment period, groups TC1 and TC2 having *B. officinalis* extracts at a dose of 150 and 300 mg/kg, respectively, showed significant weight loss, as compared to compared to TP (pathological control). Results are summarized in Table-9.

TABLE 9

Average body weight of rats during 12 weeks of treatment period.

| Groups | Average Body Weight (g) |
| --- | --- |
| Control (TA) | 376 ± 2.16 |
| Pathological control (TP) | 431 ± 2.68 |
| Orlistat (100 mg/kg) (TO) | 356 ± 4.63 |
| Sibutramine (5 mg/kg) (TS) | 361 ± 6.43 |
| *B. officinalis* extract (150 mg/kg) (TC1) | 368 ± 2.39 |
| *B. officinalis* extract (300 mg/kg) (TC2) | 381 ± 3.90 |

Lipid Profile

The group TC2 (*Borago officinalis* extract at dose of 300 mg/kg) showed a reduction in total serum cholesterol, triglyceride, HDL, and LDL level in comparison to TP (pathological control). Whereas, a significant improvement in VLDL level was observed for TC1 group (*Borago officinalis* extract at dose of 150 mg/kg) when compared with the TP, as shown in Table-10, and depicted in FIGS. 9-12, and 13.

TABLE 10

Biochemical parameters after 12 weeks of treatment in serum of normal and obese experimental rats.

| Groups | Cholesterol (mg/dL) | Triglycerides (mg/dL) | HDL (mg/dL) | LDL (mg/dL) | VLDL (mg/dL) |
|---|---|---|---|---|---|
| Control (TA) | 64 ± 2.62 | 67 ± 0.09 | 45 ± 0.56 | 10 ± 1.36 | 13 ± 2.04 |
| Pathological control (TP) | 81 ± 0.18 | 200 ± 0.05 | 44 ± 0.31 | 22 ± 1.43 | 12 ± 3.47 |
| Orlistat (100 mg/kg) (TO) | 68 ± 3.66 | 52 ± 0.16 | 52 ± 3.04 | 15 ± 0.41 | 9 ± 0.87 |
| Sibutramine (5 mg/kg) (TS) | 65 ± 0.13 | 51 ± 0.19 | 59 ± 0.16 | 14 ± 0.68 | 9 ± 0.8 |
| B. officinalis extract (150 mg/kg) (TC1) | 56 ± 0.59 | 88 ± 0.08 | 39 ± 0.21 | 16 ± 1.22 | 17 ± 0.44 |
| B. officinalis extract (300 mg/kg) (TC2) | 55 ± 0.64 | 61 ± 0.11 | 40 ± 0.25 | 15 ± 1.07 | 12 ± 0.58 |

Fasting Blood Glucose Levels

Figure 14:
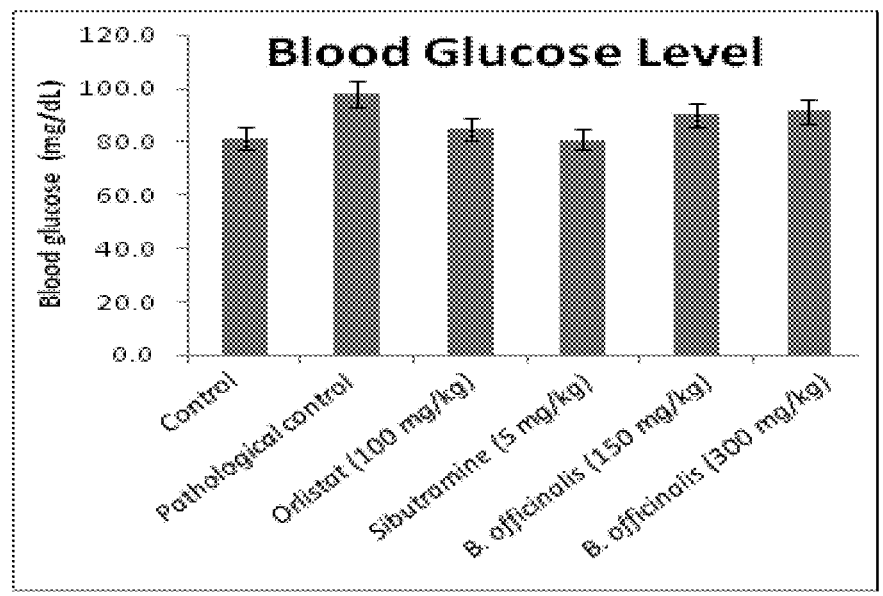
FIG. 14 depicts fasting blood glucose levels after 12 weeks of therapeutic studies on high-fat diet induced-obese rats model with *Borago officinalis* extracts (150, and 300 mg/kg). Values are expressed as mean±SEM.

Group TC1 (*Borago officinalis* extract at dose 300 mg/kg), as well as TO and TC also reduced the fasting blood glucose levels when compared with the pathological control group, as shown in Table-11, and depicted in FIG. 14.

TABLE 11

Fasting blood glucose level after 12 weeks of treatment period in the serum of normal, and obese experimental rats.

| Groups | FBG (mg/dL) |
|---|---|
| Control (TA) | 81 ± 0.12 |
| Pathological control (TP) | 97 ± 0.14 |
| Orlistat (100 mg/kg) (TO) | 84 ± 0.17 |
| Sibutramine (5 mg/kg) (TS) | 80 ± 0.12 |
| B. officinalis extract (150 mg/kg) (TC1) | 90 ± 0.15 |
| B. officinalis extract (300 mg/kg) (TC2) | 91 ± 0.37 |

Leptin Assessment

Figure 15:
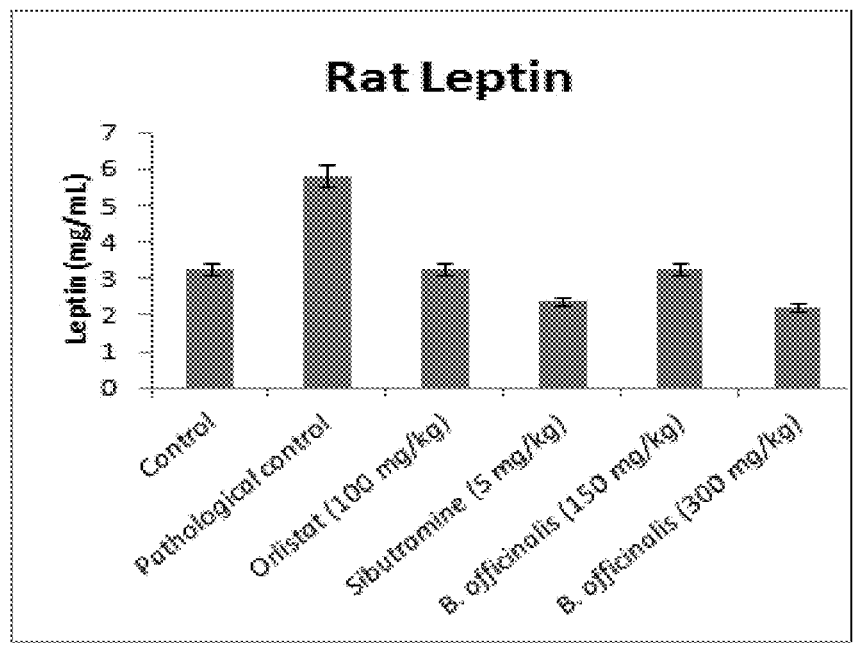
FIG. 15 depicts serum leptin levels after 12 weeks of therapeutic studies on high-fat diet induced-obese rats model with *Borago officinalis* extracts (150, and 300 mg/kg). Values are expressed as mean±SEM.

*Borago officinalis* extract at a dose 150 mg/kg (TC1), and 300 mg/kg (TC2) of body weight significantly reduced the leptin levels, when compared with the TP (pathological control), as shown in Table 12, and depicted in FIG. 15.

TABLE 12

Serum leptin dose after 12 weeks of treatment period to normal and obese experimental rats.

| Groups | Rat Leptin (mg/mL) |
|---|---|
| Control (TA) | 3.24 ± 0.12 |
| Pathological control (TP) | 5.82 ± 1.39 |
| Orlistat (100 mg/kg) (TO) | 3.26 ± 0.42 |
| Sibutramine (5 mg/kg) (TS) | 2.39 ± 1.11 |
| B. officinalis extract (150 mg/kg) (TC1) | 3.28 ± 0.21 |
| B. officinalis extract (300 mg/kg) (TC2) | 2.21 ± 0.15 |

Insulin Resistance Assessment

Figure 16:
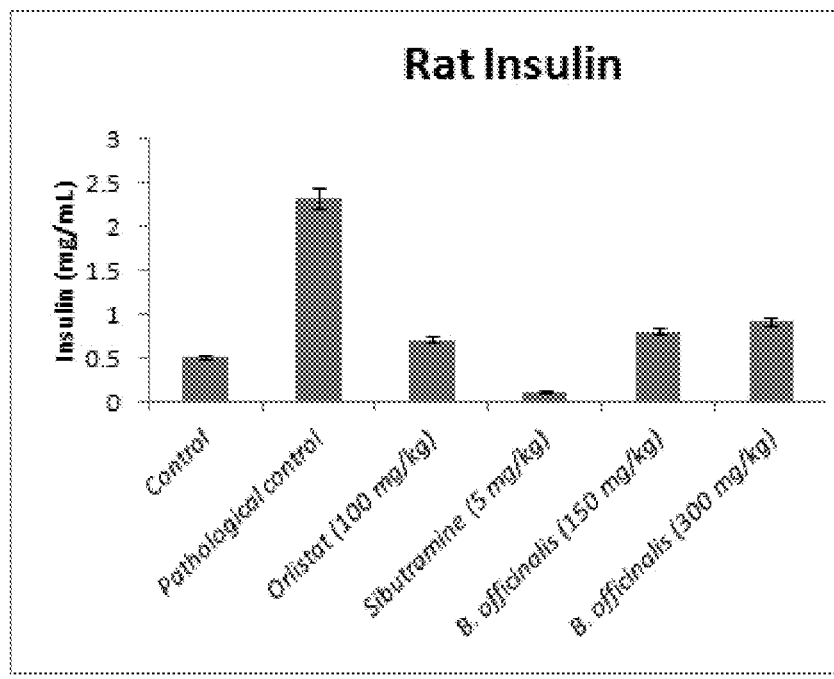
FIG. 16 depicts the serum insulin levels after 12 weeks of therapeutic studies on high fat diet induced-obese rats model with *Borago officinalis* extracts (150, and 300 mg/kg). Values are expressed as mean±SEM.

*Borago officinalis* extract both at dose of 150 mg/kg, and 300 mg/kg body weight of animal rats significantly decreased the serum insulin levels. Group TC1 showed results comparable to TA and TO groups and clearly indicate the insulin resistance reversal ability of *Borago officinalis* extract at dose of 300 mg/kg (Table-13, FIG. 16).

TABLE 13

Serum insulin estimation after 12 weeks of treatment period.

| Groups | Fasting Insulin (mg/mL) |
|---|---|
| Control (TA) | 0.52 ± 0.14 |
| Pathological control (TP) | 2.32 ± 0.92 |
| Orlistat (100 mg/kg) (TO) | 0.71 ± 0.32 |
| Sibutramine (5 mg/kg) (TS) | 0.12 ± 0.31 |
| B. officinalis extract (150 mg/kg) (TC1) | 0.81 ± 1.12 |
| B. officinalis extract (300 mg/kg) (TC2) | 0.92 ± 1.13 |

Evaluation of Renal and Liver Toxicity of *Borago officinalis* Extract

A slight reduction in the level of urea and creatinine was seen in TC1 and TC2 groups, as compared to TA (control group). The results indicated that *Borago officinalis* extract did not cause any adverse effects on renal functions.

TABLE 14

Renal toxicity assessment after 12 weeks of treatment period to normal and obese experimental rats.

| Groups | Urea (mg/dL) | Creatinine (mg/dL) |
|---|---|---|
| Control (TA) | 21 ± 1.87 | 0.46 ± 0.01 |
| Pathological control (TP) | 38 ± 1.42 | 0.47 ± 0.02 |
| Orlistat (100 mg/kg) (TO) | 30 ± 1.63 | 0.41 ± 0.01 |
| Sibutramine (5 mg/kg) (TS) | 31 ± 2.42 | 0.49 ± 0.02 |
| B. officinalis extract (150 mg/kg) (TC1) | 22 ± 2.36 | 0.30 ± 0.02 |
| B. officinalis extract (300 mg/kg) (TC2) | 13 ± 1.01 | 0.41 ± 0.01 |

The ALP and ALT levels of *Borago officinalis* extract supplemented groups (TC1 and TC2) were in a normal range and comparable to that of TO and TS groups. The elevated ALP levels indicated hepatotoxicity in obese rats (pathological control) due to the accumulation of fat in liver cells.

TABLE 15

Liver toxicity assessment after 12 weeks of treatment period in normal and obese experimental rats.

| Groups | Total Bilirubin (mg/dL) | Direct Bilirubin (mg/AL) | SGPT (U/L) | ALP (U/L) | ALT (U/L) |
|---|---|---|---|---|---|
| Control (TA) | 0.11 ± 0.004 | 0.05 ± 0.008 | 32 ± 1.17 | 85 ± 0.12 | 108 ± 0.07 |
| Pathological control (TP) | 0.17 ± 0.008 | 0.07 ± 0.004 | 42 ± 5.85 | 240 ± 0.09 | 155 ± 0.08 |
| Orlistat (100 mg/kg) (TO) | 0.13 ± 0.004 | 0.06 ± 0.008 | 48 ± 6 | 129 ± 0.19 | 108 ± 1.44 |
| Sibutramine (5 mg/kg) (TS) | 0.15 ± 0.01 | 0.03 ± 0.004 | 38 ± 3.34 | 116 ± 0.14 | 85 ± 0.009 |
| *B. officinalis* extract (150 mg/kg) (TC1) | 0.14 ± 0.01 | 0.07 ± 0.004 | 40 ± 4.72 | 109 ± 0.08 | 123 ± 0.008 |
| *B. officinalis* extract (300 mg/kg) (TC2) | 0.16 ± 0.01 | 0.08 ± 0.004 | 57 ± 3.86 | 135 ± 0.06 | 150 ± 0.10 |

Figure 17:
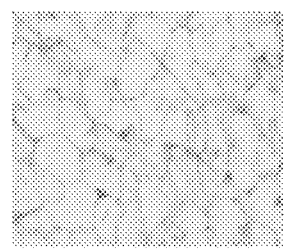
FIG. 17 depicts the histological examination of adipose tissues (therapeutic studies group) with hematoxylin, and eosin (H & E) stainings; magnification 20×. Image (a) Control, (b) Pathological Control, (c) Standard Orlistat (100 mg/kg), (d) Standard Sibutramine (5 mg/kg), (e) *Borago officinalis* EtOH extract (150 mg/kg), and (f) *Borago officinalis* EtOH extract (300 mg/kg).
Figure 17:
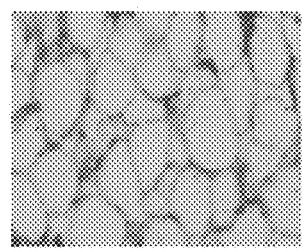
Figure 17:
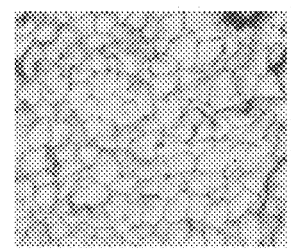
Figure 17:
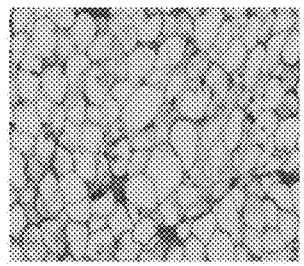
Figure 17:
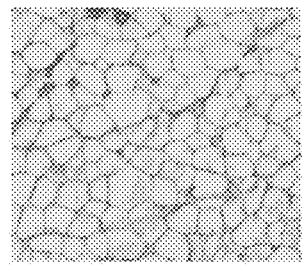
Figure 17:
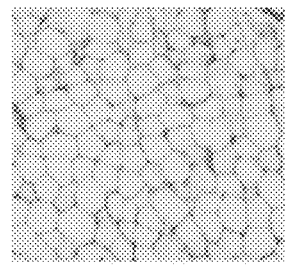

Histological Examination of Adipose Tissues:

Microscopically, the cells of adipose tissues of groups TC1 and TC2, treated with *Borago officinalis* at a dose of 150, and 300 mg/kg of body weight, respectively, were decrease in size to the normal level (FIG. 17e, and FIG. 17f) as observed through H & E staining. An excessive fat accumulation in adipocytes of pathological control group was observed clearly (FIG. 17b).

Figure 18:
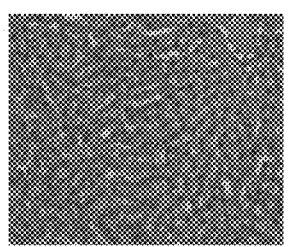
FIG. 18 depicts the histological examination of liver tissues with hematoxylin and eosin (H & E) staining; magnification 20×. Image (a) Control, (b) Pathological control, (c) Standard Orlistat (100 mg/kg), (d) Standard Sibutramine (5 mg/kg), (e) *Borago officinalis* EtOH extract (150 mg/kg), and (f) *Borago officinalis* EtOH extract (300 mg/kg).
Figure 18:
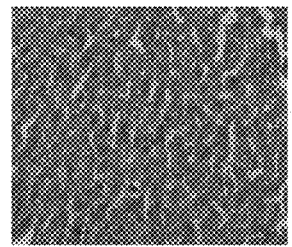
Figure 18:
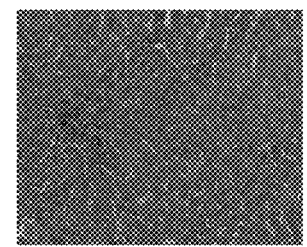
Figure 18:
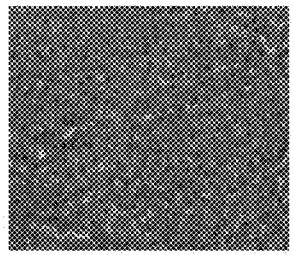
Figure 18:
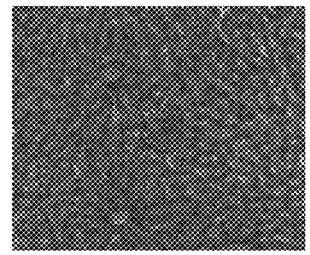
Figure 18:
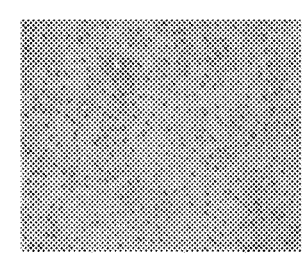

Histological Examination of Liver:

Hepatic morphological changes were examined microscopically with H & E staining. An excessive fat accumulation was seen in hepatocytes of TC (pathological control group) as compared to Orlistat and Sibutramine groups. Both TC1 (treated with *Borago officinalis* at a dose of 300 mg/kg group), and as TC2 (*Borago officinalis* at a dose of 150 mg/kg) group showed results comparable to that of control group, indicating that *Borago officinalis* also decreasing the accumulation of fats in liver. With the help of liver cell images, it was concluded that severe steatosis occurs only in pathological control group, as shown in FIG. 18.

What is claimed:

1. A method for treating insulin resistance in a human in need thereof consisting essentially of administering to said human in need thereof an oral dose of 150 mg/kg or 300 mg/kg of an ethanolic extract of *Borago officinalis*, sibutramine, and orlistat to said human in need of treatment, wherein insulin resistance is reduced by an increase in insulin sensitivity in a metabolic disorder in said human in need thereof.

* * * * *